United States Patent [19]

Licoppe et al.

[11] Patent Number: 5,405,481
[45] Date of Patent: Apr. 11, 1995

[54] GAS PHOTONANOGRAPH FOR PRODUCING AND OPTICALLY ANALYZING NANOMETRE SCALE PATTERNS

[76] Inventors: Christian Licoppe, 23 rue Lemercier, 75017 Paris; Marcel Bensoussan, 881 Caus Aquileine, 92100 Boulogne, both of France

[21] Appl. No.: 989,130

[22] Filed: Dec. 11, 1992

[30] Foreign Application Priority Data

Dec. 13, 1991 [FR] France .................. 91 15496

[51] Int. Cl.⁶ ............................. B23K 26/00
[52] U.S. Cl. ...................... 156/345; 156/626; 156/643; 156/646; 118/712; 118/722
[58] Field of Search ........... 156/626, 646, 345, 643; 118/712, 723 R, 722; 427/586, 582–584

[56] References Cited

U.S. PATENT DOCUMENTS

| | | | |
|---|---|---|---|
| 4,564,736 | 1/1986 | Jones et al. | 219/121.6 |
| 4,611,919 | 9/1986 | Brooks, Jr. et al. | 156/626 X |
| 4,930,439 | 6/1990 | Sato et al. | 118/723 |
| 4,960,495 | 10/1990 | Mori et al. | 156/643 X |
| 4,964,940 | 10/1990 | Auvert et al. | 156/345 |
| 5,062,364 | 11/1991 | Lewis et al. | 101/467 |

FOREIGN PATENT DOCUMENTS

| | | |
|---|---|---|
| 64003/90 | 4/1991 | Australia . |
| 0196346 | 10/1986 | European Pat. Off. . |
| 2623820 | 6/1989 | France . |
| 2651332 | 3/1991 | France . |
| 260125 | 12/1985 | Japan . |
| 62039 | 3/1990 | Japan . |
| 2212819 | 8/1989 | United Kingdom . |

*Primary Examiner*—Thi Dang

[57] ABSTRACT

Gas photonanograph for the production and optical analysis of nanometer scale patterns. The photonanograph has a gas expansion chamber equipped with a gas supply for producing patterns and provided at a first end with microcapillaries for the discharge of the gas, an optical fibre, which is sharp at a first end and which is to be positioned facing the sample to be treated, a light source coupled to the second end of the optical fibre, the latter being transparent to the light emitted by the light source, and detecting and processing apparatus for monitoring a light signal reflected by the sample. The photonanograph permits the localized etching or deposition of materials for microelectronics or microoptoelectronics.

22 Claims, 2 Drawing Sheets

GAS PHOTONANOGRAPH FOR PRODUCING AND OPTICALLY ANALYZING NANOMETRE SCALE PATTERNS

DESCRIPTION

The invention relates to an apparatus for producing by the gas route and for optically analyzing nanometer patterns. This apparatus will be referred to hereinafter as a gas photonanograph. The invention is more particularly applicable in the field of producing integrated circuits used in microelectronics, microoptoelectronics and integrated optical systems.

The development of integrated circuits is moving ever further towards the reduction of sizes and the increase in the integration density. Moreover, access to submicron dimensions provides a possibility of exploiting new quantum effects in original equipment.

The overall dimension, cost and complexity factors of nanoproduction methods (nanometer scale production) would appear to increase in inverse ratio to the size of the apparatuses, so that it is important for industrial applications to provide nanolithography, nanoetching and nanoproduction methods limiting the said factors.

Moreover, with these size scales, the display and evaluation in situ of the properties of the structures produced become difficult problems. It is therefore of very considerable interest to design versatile experimental tools in order to simultaneously ensure the functions of the production, visual display and analysis, more particularly the analysis of the optical properties of the structures, whose dimensions are approximately one nanometer (called nanostructures).

The known methods for the production of submicron equipment can be subdivided into two classes, a first class using focused particle beams and a second class using submicron points or tips moved to within submicron distances from the sample.

1) Within the first class, a distinction can be made between different methods as a function of the particle type used.

Within said first class, the most widely used methods employ short wavelengths, UV and X optical beams, electron beams or ion beams, cf. T. H. P. Change et al, "Nanostructure Technology", IBM Journal of Research and Development 32 (4), pp 462-493, 1988.

UV lithography by projection or holography is relatively simple and reliable up to object sizes of approximately 0.2 um. Unfortunately, for smaller object sizes, it is necessary to make use of methods employing X, ion or electron beams, the latter being the most widely used, cf. S. Mackie et al, "Materials and processes for nanometer lithography", Solid State Technology, pp 117-122, 1985.

Within the said methods, a distinction must also be made on the one hand between nanolithographies operating by localized reactions on intermediate photosensitive resins, either by projecting through masks, or by direct writing, and on the other hand reactive medium etching and deposition, in which case the particle beam focused on the sample directly stimulates a localized reaction in the reactive medium and the pattern is written by sequential displacement of the beam on the sample.

In these latter configurations in the reactive medium, with the exception of the very special case where the reactive elements are those forming the particle beam, one of the difficulties consists of having a reagent introduction nozzle which is sufficiently convergent to minimize the size of the area irradiated by the gases.

In general terms, X, ion and electron beam nanoproduction methods are difficult and costly, more particularly requiring particle sources of an extreme sophistication. Furthermore, when they do make it possible to carry out in situ analyses of the nanopatterns which they have made it possible to produce, this is only the case under structural angles accessible to tools such as X microscopy or electron microscopy, i.e. a spatial description of the patterns with a nanometer resolution and optionally an analysis of the crystalline quality by diffraction. This constitutes a severe limitation to the analysis procedures, when the most interesting properties of nanostructures are of the electron or optical order. 2) The development of tunneling microscopy using a submicron point or tip has opened the way to a second class of nanoproduction. By checking the voltage of the tunneling point, it is possible to act locally on photosensitive resins (cf. M. A. McCord et al "Lift-off metallization using PMMA exposed with a scanning tunneling microscope", Journal of Vacuum Science and Technology, B4, p 86, 1986), to deposit metals in a metal organic environment reactive to the electrons emitted by the tunnel effect (cf. E. E. Ehrichs et al, "Direct writing with the STM", Journal of Vacuum Science and Technology, A6, pp 540-543, 1988), displace atoms and induce varied modifications of the surfaces at a scale as small as the isolated atom (cf. E. J. Van Loenen et al, "Direct writing in Si with a scanning tunneling microscope", Applied Physics Letters, 55, (13), pp 1312-1314, Sep. 1989). Moreover, by modulating the current produced by tunneling, the tunneling microscope permits electron order in situ analyses.

The intensity of the electric current emitted by tunneling is limited by the electrical resistance of the sample to be analyzed. The main limitation of this method is consequently that it can only be carried out on highly doped semiconductor, metal or conductive substrates. In the case of semiconductor substrates, a spectroscopic analysis of the spatial distribution of the full and empty energy states is possible in situ by modulation of the tunneling current.

Apart from tunneling microscopy, there are other microscopies referred to as "near field", such as in particular near field optical microscopy described by D. Pohl "Scanning near-field optical microscopy", Advances in Optical and Electron Microscopy, published by C. R. J. Sheppard and T. Mulvey, Academic Press, London 1991, pp 1 to 29.

In this method, a silica fibre sharpened by mechanochemical treatment (cf. in this connection D. Courjon et al, "Scanning tunneling optical microscopy", Optical Communications, vol. 12, pp 23-28, 1989) or a hollow micropipette (cf. A. Harootunian et al, "Super-resolution fluorescence near-field scanning optical microscopy", Applied Physics Letters, 49, 11, pp 674/6, 1986) is brought by piezoelectric displacements into the vicinity of the sample to be analyzed in a proximity controlled to within a fraction of a nanometer. The radius of curvature of the micropipette or the fibre point or tip is approximately 10 nanometers.

This apparatus can operate in the illumination-reflection mode, in which the incident light and the reflected light both pass through the tip, as described in the aforementioned document by A. Harootunian, and a light collection mode, in which the illumination takes place from the side or the rear of the sample, when the latter is transparent and when the tip is only used for near field collection of part of the reflected or transmitted light (as described by U. C. Fisher and D. W. Pohl, "Observation of single particles plasmons by near-field optical microscopy", Physical Review Letters, vol. 62 (4), pp 458–461, 1989).

It can also operate in an optical tunneling mode, in which the tip is coupled to the evanescent wave, which undergoes total multiple reflections within the transparent substrate to be analyzed, as described by E. Betzig et al, "Collection mode near-field scanning optical microscopy", Applied Physics Letters, 51 (25), pp 2088–2090, Dec. 1987.

As other documents relating to a near field microscope, reference can be made to French patent applications FR-A-2 651 332, FR-A-2 653 906 and FR-A-2 654 212.

Whatever the operating mode used in near field microscopy, the tip at present makes it possible to carry out a microscopic analysis with a resolution to within 10 nm and spectroscopic measurements in the infrared near and visible optical range with the same spatial resolution.

In parallel, known gas phase deposits assisted by electromagnetic, pyrolytic or photolytic radiation at present have a spatial resolution limited by the wavelength of the beam used, as a result of the diffraction limit, which makes it necessary to work in the remote ultraviolet in order to obtain a nanometer scale resolution of the pattern.

The invention relates to an apparatus for the production by the gaseous route and optical analysis of nanometer scale patterns making it possible to obviate the aforementioned disadvantages.

This apparatus is intended for the deposition and etching of nonometer patterns and their in situ checking. In particular it makes it possible to obviate the wavelength limitation for radiation-assisted etching and deposition and to decorrelate the resolution and wavelength of the exciting beam. Thus, it makes it possible to use all spectroscopic resonances (ultraviolet, visible, infrared) associated with the chemical deposition and etching reactions independently of constraints linked with the size of the patterns, controlled by other aspects of the apparatus. By freeing the choice of radiation used from the constraints associated with the Abbe diffraction limits, the apparatus consequently offers the possibility of better optimizing the quantum efficiencies of the reactions necessary for deposition or etching.

More specifically, the invention relates to an apparatus for the production by the gaseous route and for the optical analysis of nanometer patterns on a sample, having a tight, sealed, gas expansion chamber equipped with first gas supply means for the production of patterns and having at a first end microcapillaries for the discharge of the gas, an optical fibre sharpened at a first end and which is to be positioned facing the sample to be treated, a light source coupled to a second end of the optical fibre, the latter being able to carry the light emitted by the source, as well as means for detecting and means for processing the light signal reflected by the sample.

Preferably, the apparatus also has a gas reserve chamber, equipped with gas supply means and in particular joined to the expansion chamber for forming a unitary assembly. In particular, the expansion and reserve chambers are placed end to end and coaxially. However, they could also be juxtaposed or simply separated and interconnected by a gas supply pipe.

As a result of a double integration, the apparatus according to the invention makes it possible to deposit or etch patterns of nanometer size by the gaseous route, whilst ensuring their in situ checking by the optical route.

By firstly integrating a sharp optical fibre with a gas-filled, tight enclosure provided with gas discharge microcapillaries, a stopcock and a connector for a second optical fibre outside the apparatus, a photonanograph is obtained for the nanodeposition and/or nanoetching of patterns by known photothermal and/or photolytic processes and which consequently have a double function.

By making the optical fibre integral with the enclosure from an index profile material, so that the light emitted by the sources used (ultraviolet, visible or infrared) is guided and not attenuated, it is possible for an exciting light beam to reach the sample at the same time as the reactive gas, so that on the sample surface, a photochemical reaction is only possible in near field conditions, in which the exciting light beam remains focused, whilst obtaining freedom from the diffraction limits, which occur at the wavelength scale used.

Advantageously, the sharp part of the fibre can be covered with an external coating of high reflectivity at the wavelength of the incident beam emitted by the source, with the exception of the more pointed end of the fibre, which guides the light and is located directly in front of the surface to be treated. In this way it is possible to ensure a better focusing of the irradiation beam.

Advantageously, the optical fibre integral with the enclosure has at its second end a standard connector, so that it is possible to connect thereto any system consisting of a light source plus an exit fibre. During the use of the apparatus, it is then advantageously possible to change the nature of the light irradiating the sample as a function of requirements. Thus, an optical coupling fibre can be fitted to the connector in order to couple the sharp optical fibre to a random light source. However, it is also possible to only use a single optical fibre between the sample and the light source. Advantageously, the microcapillaries are arranged in a ring around the optical fibre and are in particular oriented obliquely with respect to the optical fibre, so as to obtain a homogeneous distribution of the reactive gases in the vicinity of the fibre tip and just above the sample.

The passage diameter of the gases, ensured by the microcapillaries in the vicinity of the optical fibre tip, can typically be made four orders of magnitude smaller than the conventional pipe and the volume of the expansion and reserve chambers to be filled with gas can be made five orders of magnitude smaller than that of the known chemical vapour deposition and etching reactor (CVD).

Thus, with the apparatus according to the invention, an active gas charge of a few dozen $cm^3$ (e.g. 10 to 100 $cm^3$) at a pressure of a few hundred kilopascals (e.g. 2 to $10 \times 10^3$ kPa) is sufficient for ensuring the same total gas pressure and flow rate conditions as in conventional low pressure CVD etching or deposition using a 10 liter gas cylinder or bottle containing $2 \times 10^4$ kPa supplying gas to a 1 $dm^3$ reactor at a flow rate of 100 $cm^3/s$ and a pressure of approximately 1 kPa.

Therefore the gas supply-optical fibre assembly can be integrated into an autonomous apparatus, which has dimensions of a few centimeters, thus economizing on all gas injection systems used in CVD etching or deposition and consequently leading to significant space and cost savings as well as safety improvements compared with a conventional reactive gas etching or deposition apparatus.

The gaseous charge can either be a system, whose content can be replenished as often as necessary, or as a sealed system with the possibility of changing at random and separately the point system and the gaseous charge.

The apparatus according to the invention has the advantage, compared with prior art CVD equipment, of being able to work with light sources, laser sources or even lamps emitting in a complete wavelength range from the infrared to the ultraviolet and of providing access to all possible light signal processing types. Thus, it obviates numerous technical problems linked with the development of X, electron or ion sources having the degree of stability and brightness necessary for this type of application.

The second integration level of the apparatus according to the invention is to use the photonanograph as a near field optical microscope, whose point, used for imaging, is constituted by the point or tip of the optical fibre of the photonanograph. This optical microscope can function in the reflection-absorption mode, the collection mode or the optical tunneling mode.

Completely integrated with its displacement system for development on the sample and the control of the source, in the present state of the art, the apparatus can be reduced to a space less than 1 dm$^3$ and can therefore easily be inserted in numerous experimental configurations, particularly as, with its integrated gaseous charge, it is perfectly autonomous.

The main fields of use of the apparatus according to the invention are writing by pyrolytic and photolytic material deposits of a localized nature, in the vapour phase, and reactive photoablation, whereby it is optionally possible to combine photolytic deposition and photoablation.

The invention also relates to a localized, direct pyrolytic deposition process of a material on a sample using the aforementioned apparatus and which consists of irradiating the sample by a light beam emitted by the light source and transmitted by the optical fibre in order to heat the sample and simultaneously subject the latter to the action of gaseous precursors of said material, via the microcapillaries.

In particular, said pyrolytic deposition process can apply to the deposition of silicon, germanium, III–V or II–VI compound dielectrics, the gaseous precursors being hydrides and/or metalorganics. For the deposition of silicon, use is e.g. made of silane ($SiH_4$), for the deposition of germanium, use is made of germane or trimethyl germanium (TMGa), for the deposition of GaAs, use can be made of a mixture of TmGa and $AsH_3$, for the deposition of ZnSe, use can be made of a mixture of trimethyl zinc and $SeH_3$, etc.

The invention also relates to a process for the localized deposition of a material and which is photochemically assisted using the aforementioned apparatus. In particular, this process can be applied to the local deposition of silica using as gaseous precursors silane and oxygen, or the local deposition of silicon nitride using as the gaseous precursors silane and ammonia.

The invention also relates to a process for the localized etching of a material and which is photochemically assisted, which uses the aforementioned apparatus. In particular, the reactive gases used for etching are based on halogens.

It is also possible to consider applications of the nanolithographic type in sufficiently thin photosensitive resin layers, with the possibility of carryiing out the resin irradiation and development in a single stage e.g. using a lift-off process.

The invention also relates to a process for the direct production of photosensitive resin patterns using the aforementioned apparatus.

Moreover, the apparatus has the at present unique capacity of simultaneously ensuring the production of nanopatterns and their observation by optical methods and in particular spectroscopic methods (UV, visible or IR).

The apparatus according to the invention is also applicable to any surface type (e.g. insulating or semiconductor) and not only to conductive surfaces, which have hitherto required the use of an electron tunneling microscope.

The apparatus according to the invention is usable with a wide range of gases or gaseous mixtures and with a very wide range of optical sources (lamp or laser emitting in the UV, visible or infrared). It can be applied to all etching and deposition types (metals, semiconductors or insulants) and to all types of substrates (glasses, metals, semiconductors), which may or may not be covered by a photosensitive resin.

The invention is described in greater detail hereinafter relative to non-limitative embodiments and with reference to the attached drawings, wherein show:

BRIEF DESCRIPTION OF THE DRAWINGS

Figure 1:
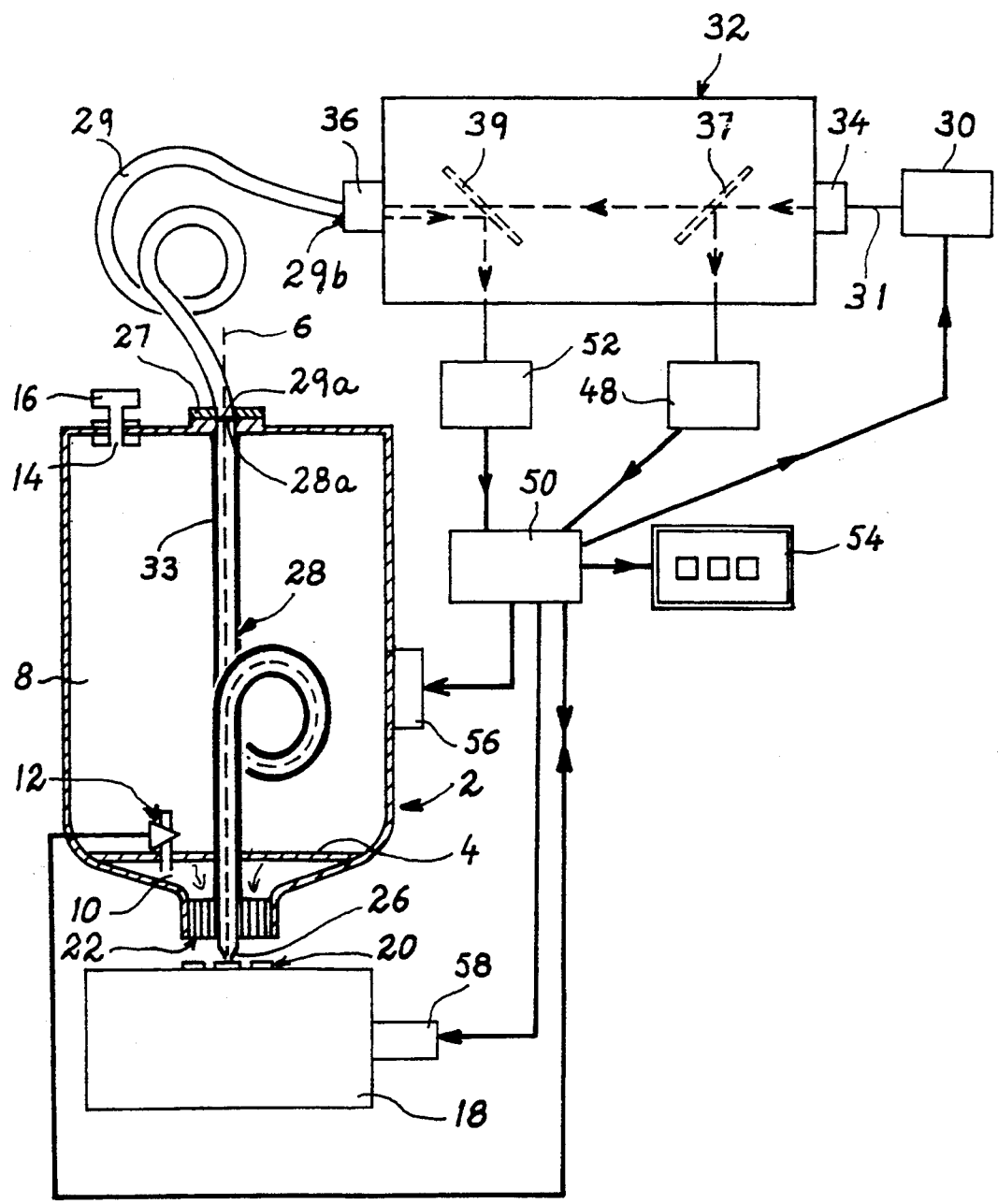
FIG. 1 Diagrammatically a gas photonanograph according to the invention.
Figure 2:
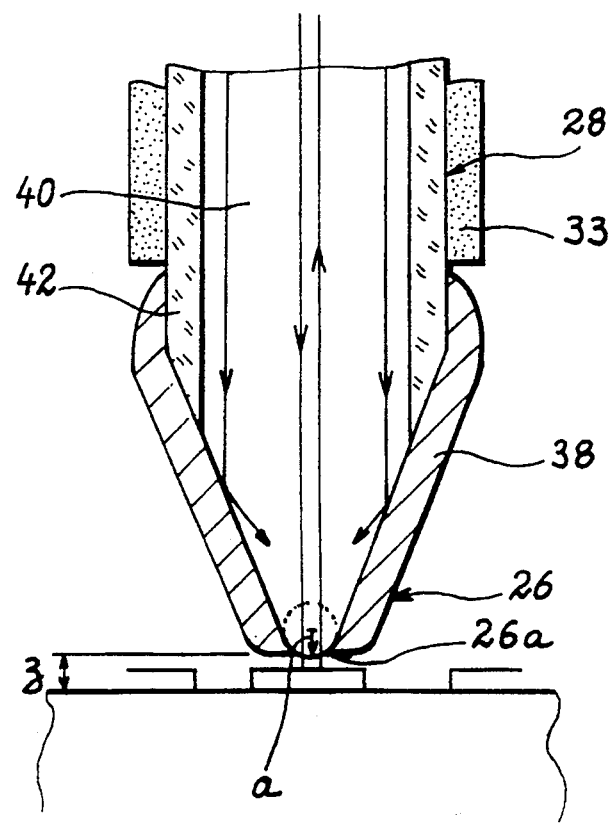
FIG. 2 Diagrammatically in the form of a more detailed section, the metallized point or tip of the optical fiber of the apparatus of FIG. 1.
Figure 3:
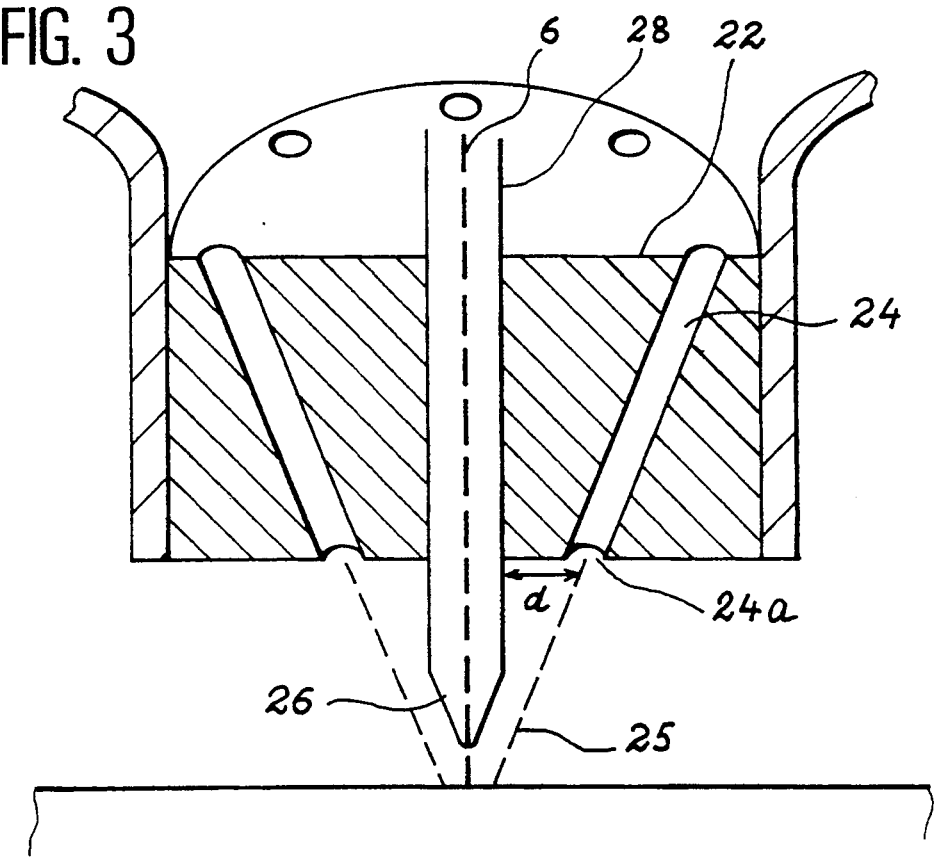
FIG. 3 In perspective and detail, the arrangement of the microcapillaries of the apparatus of FIG. 1.

According to FIGS. 1 to 3, the apparatus for the production and analysis of nanometre patterns according to the invention has a tight, sealed reservoir 2 in the form of a bottle, equipped in its lower part with a wall 4 arranged perpendicular to the axis 6 of symmetry of the reservoir and defining two coaxial, integral gas chambers, which are joined end to end, namely an upper reserve chamber 8 and an expansion chamber 10. A leak valve 12 fitted to the wall 4 makes it possible to link the chambers 8 and 10 and regulate the gas flow rate leaving the apparatus. The gas reserve chamber 8 defines a gas volume higher than that of the expansion chamber 10. The reservoir 2 is equipped in its upper part with an orifice 14 for the filling of the chamber 8, which is sealed with a plug 16.

These two chambers 8 and 10 ensure the functional autonomy of the apparatus according to the invention and make it possible to regularly replenish the reactive gas. For example, the reservoir 2 can contain 20 to 50 $cm^3$ of reactive gas under a pressure of $10^3$ Pa.

The end or neck of the reservoir 2 to be positioned facing the sample 18 which is to be etched or locally covered with a material 20 is provided with a plug 22 having microcapillaries 24 for the discharge of the reactive gas contained in the expansion chamber 10. These microcapillaries 24 are arranged in the form of a ring in order to ensure a homogeneous distribution of the gas under overpressure in the vicinity of the sample 18.

In particular, the longitudinal axes of these microcapillaries 24 (FIG. 3) are inclined with respect to the reservoir axis 6 in order to direct gas jets 25 towards the tip or point 26 of an optical fibre 28 traversing the reservoir 2 and the plug 22. Advantageously, the fibre is located in the reservoir, provided that its tip 26 projects out of the plug 22.

The optical fibre is only joined to the reservoir 2 by its ends. The end 28a of the fibre 28, opposite to the tip 26, is connected at the intake of the reservoir 2 to an optical fibre connector 27, which is fitted outside the reservoir 2.

Advantageously the fibre 28 is covered with an opaque flexible sheath 33, which protects it against the reactive gases in the chambers 8 and 10. The optical fibre tip 26 is obtained by a mechanochemical treatment and has a rounded end 26a with a radius of curvature a of 30 to 100 nm.

The ring-like arrangement of the microcapillaries around the tip 26 ensures a homogeneous, symmetrical gas flow. Using 25 microcapillaries each with a cross-section of 200 $\mu m^2$ and whose ends 24a facing the sample are placed at a distance d of 1 cm from the optical fibre 28, a gas pressure $10^3$ Pa and a bonding coefficient of 0.01 of the gas atoms to the sample 18, deposition conditions are obtained such that one material monolayer 20 per second is deposited.

The leak valve 12 and the expansion chamber 10, placed between the gas reserve chamber 8 and the microcapillaries 24, make it possible to check or control the gas pressure in the capillaries and modulate the gas flow reaching the sample 18.

The end 28a of the optical fibre 28 is connected, via the optical fibre connector 27, to a first end 29a of a second fibre. The other end 29b of said second fibre is coupled to a light source 30, of the laser diode or lamp type. Coupling is ensured by an optical assembly 32 having an entrance collimating lens 34 for collimating the incident beam 31, two beam-dividing cubes 37, 39 inclined by approximately 45° with respect to the incident beam 31 and an exit focusing lens 36 for focusing the incident beam at the end 29b of the optical fibre 29. The use of an optical coupling fibre 29 makes it possible to rapidly change the said fibre and therefore the light source.

The optical fibres 28 and 29 must be transparent to the emission wavelength of the source 30, said wavelength being suitable for the particular envisaged application. In particular, the optical fibres are made from silica. They are e.g. constituted by a core surrounded by an index profile layer ensuring an effective guidance and optionally a protective sheath.

In FIG. 2, the references 40 and 42 respectively indicate the core and index profile layer of the fibre 28.

However, the optical fibre 28 is covered (FIG. 2) on its thinned part 26, with the exception of its narrowest end 26a, over a region having the size of the radius of curvature a, by a metal coating 38, so as to only allow light to pass out of the fibre by its end 26a. Said coating 38 is e.g. constituted by a chromium layer ensuring the adhesion, covered with a silver layer and deposited by evaporation. The metal coating 38 ensures the confinement of the light in the thinned part 26, where the fibre no longer guides light.

The beam dividing tube 37 makes it possible to sample part of the incident light 31 with a view to checking the same. The sampled part is consequently supplied to a detector 48 of the photodiode type transforming the light signal into an electrical signal. Said detector is connected to a processing circuit 50 of the microprocessor type which, as a function of the signal emitted by the detector 48, modifies the emission characteristics of the source 30. This non-essential system is used for regulating the intensity of the light traversing the optical fibre 28.

The other part of the incident beam is passed to the sample to be treated via the optical fibre 29, with a view to the treatment (deposition or etching) of the material 20 and/or the control of said material.

The optical fibre 29 serves not only to transmit light informations from the source 30 to the sample 18, but also to transmit the light reflected by the sample 18. The light from the sample is received, via the lens 36, by the second beam dividing cube 39. The light reflected by said cube 39 is then detected by a detector 52 of the photodiode type, which transforms the reflected light signal into an electrical signal.

This detector 52 is connected to the processing circuit 50 with a view to checking the local deposition or etching carried out on the sample 18. Moreover, the circuit 50 controls a display screen 54 with a view to a possible display of the material 20 which has been deposited or etched. In addition, the processing circuit 50 controls the opening and closing of the valve 12, so as to regulate the reactive gas flow rate and pressure in the expansion chamber 10 and in the microcapillaries.

For display purposes, a development system on the sample must be provided and can consist of one or more piezoelectric ceramics 56 integral with the reservoir 2 and controlled by the processing circuit 50 and optionally one or more piezoelectric ceramics 58 integral with the sample and which are also controlled by the processing circuit 50.

The beam dividing cube 39 at the entrance of the optical fibre 29, as a result of the polarization, makes a distinction between the light reflected by the sample 18 and the incident light. The photodiode 52 which receives said reflected light, measures the light intensity thereof and the processing circuit 50 deduces therefrom the distance z separating the end 26a of the tip 26 and the sample 18.

By acting on the voltages applied to the piezoelectric ceramics 56 or 58, the distance z is varied. At approximately 10 nanometers from the sample, the light intensity of the reflected light increases exponentially.

The apparatus according to the invention can be used for a local pyrolytic material deposit. It makes it possible to check the temperature rise induced on the sample 18 by an intense laser beam 31 (e.g. infrared $CO_2$ or visible argon power laser) traversing the fibre 28, combined with a heating temperature of the sample 18 appropriate for stimulating a localized reaction on the surface of the sample 18. The local temperature rise on the sample is very appropriate for the localized deposition of silicon, dielectric or III-V compounds from hydrides or metal-organics.

The gas photonanograph according to the invention can be inserted in a vacuum reaction chamber for carrying out vacuum material deposition or etching operations.

Advantageously, the pressure in the reaction chamber is such that the average free path of the molecules in the chamber is smaller than the distance z separating the end 26a from the point of the sample (typically approximately $10^4$ Pa).

Thus, the apparatus according to the invention can be used for a local etching or deposition of a material in photochemically assisted form. In this case, the incident beam 31 is constituted by an e.g. ultraviolet exciting beam. The photoassisted reaction can only then occur on the illuminated sample surface. In particular, a localized silica photodeposit can be obtained from a mixture of silane and oxygen.

In this particular case, the gas photonanograph according to the invention is inserted in an enclosure containing an oxygen atmosphere and the reservoir 2 is filled with silane in order to pass the latter on to the sample. The UV radiation emitted by the source is advantageously between 160 and 200 nm. Typically, the light source is constituted by an excimer laser emitting at 193 nm. This wavelength is absorbed by the oxygen, unlike the silane. The silane reacts on the photoexcited species of the oxygen, only on the sample surface. Under these conditions, there is a localized photodeposition of silica nanopatterns. The characteristic size of the patterns is of the same order of magnitude as the radius of curvature a of the end 26a of the tip, plus twice the diffusion length of the gas molecules.

With the apparatus according to the invention, it is also possible to carry out localized, photochemically assisted deposits of metals. In this case, use is made of the displacement of resonance lines of a molecule of the reactive gas which can be adsorbed on the sample. By specifically exciting the resonance lines of the adsorbed phase, a deposition reaction is only produced on the illuminated sample surface.

This localized deposition process can in particular be used for repairing integrated circuits or for producing resin masks for etching or for ion implantation.

The apparatus according to the invention can also be used for nanoetching. Thus, it is possible to avoid the stage of transferring the photosensitive resin mask, which in nanolithography is one of the success limiting factors. In this case, there is a localized chemical etching of the material 20 by exposing it to reactive gases, more particularly based on iodine, bromine, fluorine or chlorine, as a function of the nature of the material to be etched, whilst locally subjecting it to an ultraviolet beam 31, via the sharp optical fibre.

The apparatus according to the invention can also be used for nanolithography by direct writing of patterns on a photosensitive resin. It offers the possibility of carrying out at the same time the irradiation and developing of the resin by the reactive route.

Thus, the resin is irradiated by the light beam 31 passing out of the optical fibre tip 26 and developing of the patterns takes place by the gas passing out through the microcapillaries. It is in particular possible to use an ultraviolet light source emitting at around 200 nm for irradiation and oxygen as the etching gas for the photosensitive resins.

Using the same tip 26, the sample 18 is illuminated with visible or infrared light emitted by the source 30, as a function of the sought control or checking type for the deposit. Thus, by moving the tip 26 above deposited or etched nanometer patterns, it is possible to analyze either morphologically (invisible light) or spectroscopically (in infrared light) the patterns immediately following their deposition or etching. The results of this analysis can be displayed on the screen 54.

We claim:

1. Apparatus for producing by gaseous technique and for optically analyzing nanometer patterns on a sample, said apparatus including a tightly sealed gas expansion chamber having first and second ends, said chamber being operably connected to a first gas supply means for supplying gas into the chamber for use in producing patterns, microcapillaries at the first end of the chamber for discharging gas from the chamber, an optical fibre having first and second ends arranged for transmitting incoming light from an incident beam light source to a sample to be treated, said optical fibre second end being coupled to said light source for transmitting incoming light to said first fiber end facing said sample, said optical fibre including a sharpened tip having a radius of curvature of less than 100 nm at said first end and being spaced from the sample a distance less than the wavelength of the incoming light, and means for detecting and means for processing a light signal reflected from the sample.

2. Apparatus according to claim 1, characterized in that the microcapillaries are arranged in a ring around the optical fibre tip.

3. Apparatus according to claim 1, characterized in that the microcapillaries are inclined with respect to the optical fibre tip.

4. Apparatus according to claim 1, characterized in that the expansion chamber is sealed at its first end by a plug providing said microcapillaries and in that the first end of the optical fibre extends through the plug and its tip projects out of the plug.

5. Apparatus according to claim 1, further comprising a gas reserve chamber equipped with a second gas supply means, said gas reserve chamber being connected to said expansion chamber.

6. Apparatus according to claim 5, characterized in that the two chambers are integral and are linked via said first gas supply means.

7. Apparatus according to claim 6, characterized in that the two chambers are arranged end to end and coaxially and are linked via said first gas supply means.

8. Apparatus according to claim 1, characterized in that means for dividing the incident beam from the light source are provided so as to produce a first light beam providing said incoming light used for analysis and/or processing the sample and a second beam for checking the beam emitted by the source.

9. Apparatus according to claim 1, characterized in that display means connected to the processing means are provided.

10. Apparatus according to claim 1, characterized in that a portion of the optical fiber adjacent said sharpened tip is covered by an outer coating having high reflectivity at the wavelength of the incident beam from the light source.

11. Apparatus according to claim 1, characterized in that the optical fiber is partly covered with a metal coating.

12. Apparatus according to claim 5, wherein the optical fiber for transmitting incoming light extends through the expansion chamber and reserve chamber and is covered over its length, within the expansion and reserve chambers, with a sheath, which protects the optical fiber against the reactive gases located there.

13. Apparatus according to claim 1, wherein the second end of the optical fiber is provided with an optical fiber connector and a coupling optical fiber extends between said connector and said light source to ensure the coupling of the optical fiber to the light source.

14. Apparatus according to claim 1, characterized in that means are provided for performing a relative displacement between the optical fiber tip and the sample for focusing purposes.

15. Apparatus according to claim 1, characterized in that the apparatus constitutes an autonomous assembly.

16. Process for the direct, local pyrolytic deposition of a material on a sample, characterized in that the process includes using the apparatus according to claim 1, for irradiating a sample with a light beam emitted by the light source and transmitted by the optical fiber for heating said sample and simultaneously subjecting the sample to the action of gaseous precursors of said material, via the microcapillaries.

17. Process according to claim 16, applied to the local deposition of silicon, dielectric or a III–V compound, characterized in that the gaseous precursors are hydrides and/or metalorganics.

18. Process for the localized deposition of a material on a sample and which is photochemically assisted, characterized in that it consists of using the apparatus according to claim 1, exposing the sample to a light beam emitted by the light source and transmitted by the optical fiber and simultaneously exposing the sample to the action of gaseous precursors of said material, via the microcapillaries.

19. Process according to claim 18 applied to the local deposition of silica, characterized in that the gaseous precursors are silane and oxygen, in that the apparatus and the sample are placed in an oxygen atmosphere and in that the substrate is subjected to the action of silane, via the microcapillaries.

20. Process for the local etching of a material, which is photochemically assisted, characterized in that it consists of using the apparatus according to claim 1, subjecting the sample to the action of a light beam emitted by the light source and transmitted by the optical fiber and simultaneously subjecting the sample to the action of reactive gases able to etch it.

21. Process according to claim 20, characterized in that the reactive gases is a halogen.

22. Process for the production of photosensitive resin patterns, characterized in that it consists of using the apparatus according to claim 1, subjecting the resin to the action of a light beam emitted by the light source and transmitted by the optical fiber and simultaneously subjecting the resin to reactive gases able to etch it.

* * * * *

UNITED STATES PATENT AND TRADEMARK OFFICE
CERTIFICATE OF CORRECTION

PATENT NO. : 5,405,481
DATED : April 11, 1995
INVENTOR(S) : Christian Licoppe, et al.

It is certified that error appears in the above-indentified patent and that said Letters Patent is hereby corrected as shown below:

On the title page, before item [57], insert the following, attorney, agent or firm:

--Pearne, Gordon, McCoy & Granger, Cleveland, Ohio--.

Column 1, line 44, delete "Change" and insert --Chang--.

Column 2, line 16, after "order." start a new paragraph.

Column 4, line 44, after "source." start a new paragraph.

Column 6, line 6, delete "carryiing" and insert --carrying--.

Signed and Sealed this

Seventh Day of November, 1995

Attest:

BRUCE LEHMAN

*Attesting Officer*     *Commissioner of Patents and Trademarks*

UNITED STATES PATENT AND TRADEMARK OFFICE
CERTIFICATE OF CORRECTION

PATENT NO. : 5,405,481
DATED : April 11, 1995
INVENTOR(S) : Christian Licoppe et al.

It is certified that error appears in the above-indentified patent and that said Letters Patent is hereby corrected as shown below:

On the title page, insert item [73] Assignee:

--FRANCE TELECOM Etablissement autonome de droit public--.

Signed and Sealed this

Twenty-sixth Day of December, 1995

Attest:

BRUCE LEHMAN

*Attesting Officer*   *Commissioner of Patents and Trademarks*